(12) United States Patent
Kitron Kuperstein et al.

(10) Patent No.: US 9,370,190 B2
(45) Date of Patent: Jun. 21, 2016

(54) PEST REPELLENTS FROM PLANT EXTRACTS

(71) Applicant: EDEN SHIELD LTD., Misgav (IL)

(72) Inventors: Yaniv Kitron Kuperstein, Jerusalem (IL); Yonatan Eitan Menashe, Jerusalem (IL)

(73) Assignee: EDEN SHIELD LTD., Misgav (IL)

( * ) Notice: Subject to any disclaimer, the term of this patent is extended or adjusted under 35 U.S.C. 154(b) by 0 days.

(21) Appl. No.: 14/411,673

(22) PCT Filed: Jul. 4, 2013

(86) PCT No.: PCT/IL2013/050575
§ 371 (c)(1),
(2) Date: Dec. 29, 2014

(87) PCT Pub. No.: WO2014/006626
PCT Pub. Date: Jan. 9, 2014

(65) Prior Publication Data
US 2015/0189890 A1 Jul. 9, 2015

Related U.S. Application Data

(60) Provisional application No. 61/668,042, filed on Jul. 5, 2012.

(51) Int. Cl.
| *A61K 36/00* | (2006.01) |
| *A01N 65/12* | (2009.01) |
| *A61K 36/28* | (2006.01) |
| *A01N 65/00* | (2009.01) |
| *A01N 43/16* | (2006.01) |
| *A01N 45/00* | (2006.01) |

(52) U.S. Cl.
CPC ............... *A01N 65/12* (2013.01); *A01N 43/16* (2013.01); *A01N 45/00* (2013.01); *A01N 65/00* (2013.01); *A61K 36/28* (2013.01)

(58) Field of Classification Search
None
See application file for complete search history.

(56) References Cited

U.S. PATENT DOCUMENTS

| 5,736,584 | A | 4/1998 | Kunkel |
| 5,914,295 | A | 6/1999 | Hoffman et al. |
| 7,179,479 | B1 | 2/2007 | Ahn et al. |
| 8,062,676 | B2 | 11/2011 | Besendorfer |
| 2003/0124165 | A1 | 7/2003 | Vollhardt et al. |
| 2005/0019432 | A1 | 1/2005 | Baker et al. |
| 2007/0071834 | A1 | 3/2007 | Cheng et al. |
| 2007/0098570 | A1 | 5/2007 | Ohashi et al. |
| 2007/0264297 | A1 | 11/2007 | Scialdone et al. |
| 2008/0057134 | A1* | 3/2008 | Crudden ............ A61K 31/425 424/617 |
| 2010/0144888 | A1 | 6/2010 | Bessette |
| 2010/0331427 | A1 | 12/2010 | March et al. |
| 2011/0217753 | A1 | 9/2011 | Cyr |
| 2011/0300083 | A1 | 12/2011 | Yontz et al. |
| 2012/0015054 | A1 | 1/2012 | Humbert et al. |
| 2012/0076751 | A1 | 3/2012 | Bleeker et al. |
| 2012/0126024 | A1 | 5/2012 | Boyd et al. |
| 2006/1530890 | | 1/2014 | KITRON KUPERSTEIN et al. |

FOREIGN PATENT DOCUMENTS

| HU | 50592 | 12/1987 |
| JP | 2002308705 A * | 10/2002 |
| JP | 2006306796 A * | 11/2006 |
| WO | 0004780 A1 | 2/2000 |
| WO | 2007148105 A2 | 12/2007 |
| WO | 2012018152 A1 | 2/2012 |
| WO | 2012018153 A1 | 2/2012 |

OTHER PUBLICATIONS

Tunon et al, Mosquito repellents from *Achillea millefolium* L. Bulletin of the Scandinavian Society for Parasitology (1991), vol. 1, 47 p.*
Halbert et al, Plant-derived compounds and extracts with potential as aphid repellents. Annals of applied biology an international journal of the AAB (2009), vol. 154, No. 2, pp. 303-307.*
Sathiyamoorthy et al, Larvicidal activity in desert plants of the Negev and Bedouin market plant products. International Journal of Pharmacognosy (1997), vol. 35, No. 4, pp. 265-273.*
Tarawneh et al, Antifungal and antioxidant effects of extracts of some medicinal plant species growing in South Jordan. Bulletin of Faculty of Agriculture, Cairo University (2008), vol. 59, No. 3, pp. 241-248.*
Mateeva et al., "Alternative plant protection means against Tetranychus urticae Koch", Second International Symposium on Plant Health in Urban Horticulture, Aug. 2003, pp. 27-29, Berlin, Germany.
Dias et al., "Composition of essential oil and allelopathic activity of aromatic water of Aster lanceolatus Willd: (Asteraceae)", Brazilian Journal of Pharmaceutical Sciences, Jul. 2009, pp. 469-474, vol. 45, No. 3, Brazil.
Israeli Patent Office, "International Search Report and Written Opinion in corresponding International Application No. PCT/IL2013/050575", Dec. 20, 2013.

* cited by examiner

*Primary Examiner* — Qiuwen Mi

(57) ABSTRACT

A new composition for repelling pests is disclosed, wherein said composition comprises an extract produced from at least one plant chosen from the group consisting of *Achillea* spp., *Varthemia iphionoides*, *Haplophyllum turberculatum*, *Pulicaria incisa*, *Asteriscus graveolens*, *Tanacetum sinaicum*, *Verbascum* spp., *Artemisia* spp., and *Ammi visnaga*. In preferred embodiments, the extract is produced from *Achillea* spp. Methods for applying the composition are also disclosed. The composition has been shown to be effective against a variety of pests, including aphids, thrips, tomato borers, tomato leaf miners, and whiteflies.

8 Claims, 14 Drawing Sheets

PEST REPELLENTS FROM PLANT EXTRACTS

FIELD OF THE INVENTION

This invention generally relates to compositions and methods for repelling pests. More specifically, it relates to plant extract based pest repellent compositions and methods.

BACKGROUND OF THE INVENTION

Pests, particularly pest pests, remain a worldwide economic and public health concern. Agricultural damage due to pests amounts to billions of dollars annually; pests are vectors for some of the world's most deadly diseases; invasive species are of increasing concern worldwide. For these reasons, among others, control of pest populations remains a major societal concern.

One approach to control of pest populations has been the use of pesticides. Pesticides suffer from many problems, however. Synthetic pesticides, for example, tend to be poisonous, carcinogenic, or teratogenic. Since many of these pesticides are not (or are only slowly) biodegradable, the concentration of these substances in body tissues tends to increase up the food chain, a tendency that has led to disastrous effects on the populations of primary predators in many ecosystems.

There has thus been much recent effort devoted to development of "natural" means and methods of pest control, particularly those based on plant-derived chemicals such as pyrethroids. Even "natural" pesticides, including pyrethroids, suffer from the problem of pest resistance, however. As mutations that enable the pests to metabolize the active ingredient of the pesticide spread through the pest population, the effectiveness of the pesticide decreases in consequence.

In many applications, pesticidal activity is not necessarily required, and pest repellent activity is sufficient. Since the activity of pest repellents does not necessarily involve interruption of a metabolic process, repellents are inherently less likely to lead to problems of resistance. A number of disclosures of pest repellent activity of plant extracts have been made, and the ability of extracts of plants such as garlic and neem tree are well-known. Representative disclosures of plant extract-based pest repellents include U.S. Pat. No. 5,736,584 (cactus extract) and U.S. Pat. No. 7,179,479 (*Foeniculum vulgare* [fennel]); U.S. Pat. Appl. Pub. Nos. 20030124165 (*Tarchonanthus camphoratus* [camphor bush]); 20050019432 (evening primrose); 20061530890 (*Spiraea*), and 20120015054 (Euodia); and PCT Pat. Appl. Nos. WO0004780 (*Callitris columellaris* [cypress pine]), WO07148105 (*Mentha, Eucalyptus, Citrus*, Lavendula, Rosemarinus, Thymus, *Juniperus, Eugenia*), WO12018152 (oak vinegar extract), and WO12018153 (*Phellodendron* [cork tree]).

Extracts of *Achillea* spp. (yarrow) have been used in pesticidal compositions; see, for example, Hungarian Pat. No. 50592, U.S. Pat. No. 8,062,676, and U.S. Pat. Appl. Pub. Nos. 20070098570 and 20100144888.

Despite the research effort put into development of pesticidal and pest repellent plant extract based compositions, development of economically viable plant extract based pest repellents, particularly those that are useful in agricultural applications, remains a long-felt yet unmet need.

SUMMARY OF THE INVENTION

The method and composition herein disclosed are designed to meet this long-felt need. In particular, means and methods for repelling pests are disclosed that are based on extracts of plants the pest repellent activity of which is hitherto unknown.

It is therefore an object of this invention to disclose a method for repelling pests, wherein said method comprises applying an extract produced from at least one plant chosen from the group consisting of *Achillea* spp., *Varthemia iphionoides, Haplophyllum turberculatum, Pulicaria incisa, Asteriscus graveolens, Tanacetum sinaicum, Verbascum* spp., *Artemisia* spp., and *Ammi visnaga*, preferably wherein said at least one plant is chosen from the group consisting of species of the genus *Achillea*, and most preferably wherein said at least one plant is chosen from the group consisting of *Achillea santolina, Achillea fragrantissima, Achillea millefolium* and *Achillea filipendulina*.

It is a further object of this invention to disclose such a method, additionally comprising a step of preparing an extract, said step of preparing an extract comprising: placing the aerial parts of said at least one plant in a solvent for a predetermined length of time, whereby of an extract of said at least one plant in said solvent is formed; and removing from said extract solids remaining after said predetermined length of time. It is a further object of this invention to disclose such a method, wherein said solvent is ethanol of at least 95% purity. It is a further object of this invention to disclose such a method, wherein said step of placing the aerial parts of said at least one plant in a solvent for a predetermined length of time comprises placing said aerial parts of said at least one plant in 96% ethanol for about 24 hours. It is a further object of this invention to disclose such a method, wherein said step of placing the aerial parts of said at least one plant in a solvent for a predetermined length of time comprises placing about 150 g of plant material per liter of said solvent in said solvent for said predetermined length of time.

It is a further object of this invention to disclose such a method as defined in any of the above, wherein said step of applying comprises applying by a method chosen from the group consisting of spraying, dipping, coating, contacting, and brushing.

It is a further object of this invention to disclose such a method as defined in any of the above, wherein said step of applying comprises applying to a surface.

It is a further object of this invention to disclose such a method as defined in any of the above, wherein said step of applying comprises applying directly to at least part of a plant.

It is a further object of this invention to disclose such a method as defined in any of the above, wherein said step of applying comprises applying to an anti-pest net.

It is a further object of this invention to disclose such a method as defined in any of the above, wherein said step of applying comprises applying an extract that comprises a component characterized by mass spectral peaks with m/z 223, 151, 96, and 81.

It is a further object of this invention to disclose such a method as defined in any of the above, wherein said step of applying comprises applying an extract that comprises a component characterized by mass spectral peaks with m/z 94, 82, 67, 59, and 43.

It is a further object of this invention to disclose such a method as defined in any of the above, additionally comprising a step of preparing an aqueous solution of said extract in water prior to said step of applying. In some embodiments of the invention, said step of preparing an aqueous solution of said extract comprises preparing an aqueous solution in which the concentration of said extract is between 0.1% and 5% (w/v). In some embodiments of the invention, said step of preparing an aqueous solution of said extract comprises preparing an aqueous solution in which the concentration of said extract is between 0.1% and 2.5% (w/v). In some embodiments of the invention, said step of preparing an aqueous solution of said extract comprises preparing an aqueous solution in which the concentration of said extract is between 0.1% and 1.5% (w/v). In some embodiments of the invention, said step of preparing an aqueous solution of said extract comprises preparing an aqueous solution in which the concentration of said extract is between 0.1% and 0.3% (w/v). In some embodiments of the invention, said step of applying comprises applying about 60 ml of the aqueous solution as defined in any of the above per square meter of surface.

It is a further object of this invention to disclose such a method as defined in any of the above, additionally comprising a step of compounding said extract with a polymer. It is a further object of this invention to disclose such a method, wherein said polymer is polyethylene. It is a further object of this invention to disclose such a method, wherein said step of compounding said extract with a polymer comprises coextruding said extract with said polymer.

It is a further object of this invention to disclose such a method as defined in any of the above, additionally comprising a step of mixing said extract with a pesticide prior to said step of applying.

It is a further object of this invention to disclose such a method as defined in any of the above, additionally comprising a step of introducing at least one natural enemy of said pest.

It is a further object of this invention to disclose such a method as defined in any of the above, wherein said method comprises a method for repelling at least one type of pest chosen from the group consisting of aphids, tomato borers, tomato leaf miners, whiteflies, and thrips.

It is a further object of this invention to disclose a method for decreasing the rate of acquisition of resistance to a pesticide, comprising applying a mixture of said pesticide and an extract produced from at least one plant chosen from the group consisting of *Achillea* spp., *Varthemia iphionoides*, *Haplophyllum turberculatum*, *Pulicaria incisa*, *Asteriscus graveolens*, *Tanacetum sinaicum*, *Verbascum* spp., *Artemisia* spp., and *Ammi visnaga*, whereby at least some of the pests encountering said mixture are repelled by said extract in preference to ingesting said pesticide.

It is a further object of this invention to disclose a pest repellent, comprising an extract produced from at least one plant chosen from the group consisting of *Achillea* spp., *Varthemia iphionoides*, *Haplophyllum turberculatum*, *Pulicaria incisa*, *Asteriscus graveolens*, *Tanacetum sinaicum*, *Verbascum* spp., *Artemisia* spp., and *Ammi visnaga*, preferably wherein said at least one plant is chosen from the group consisting of species of the genus *Achillea*, and most preferably wherein said at least one plant is chosen from the group consisting of *Achillea santolina*, *Achillea fragrantissima*, *Achillea millefolium* and *Achillea filipendulina*.

It is a further object of this invention to disclose such a pest repellent, wherein said extract The present invention provides a method for repelling pests, wherein the method comprises a step of applying an extract produced from at least one plant selected from a group consisting of *Achillea* spp, *Varthemia iphionoides*, *Haplophyllum turberculatum*, *Pulicaria incisa*, *Asteriscus graveolens*, *Tanacetum sinaicum*, *Verbascum* spp., *Artemisia* spp., and *Ammi visnaga*.

It is another object of the current invention to disclose the method as defined in any of the above, wherein at least one plant is selected from a group consisting of species of the genus *Achillea*.

It is another object of the current invention to disclose the method as defined in any of the above, wherein the genus *Achillea* is selected from a group consisting of: (a) *Achillea santolina*; (b) *Achillea fragrantissima*; (c) *Achillea filipendulina*; (d) *Achillea millefolium* and any combination thereof.

It is another object of the current invention to disclose the method as defined in any of the above, additionally comprising a step of preparing an extract, the step of preparing an extract, comprising: (a) placing the aerial root parts of at least one plant in a solvent for a predetermined length of time, whereby an extract of at least one plant in the solvent is formed; and (b) removing from the extract solids remaining after the predetermined length of time.

It is another object of the current invention to disclose the method as defined in any of the above, wherein the solvent is ethanol of at least 95% purity.

It is another object of the current invention to disclose the method as defined in any of the above, wherein the step of placing the aerial root parts of at least one plant in a solvent for a predetermined length of time comprises placing the aerial parts of at least one plant in 96% ethanol for about 24 hours.

It is another object of the current invention to disclose the method as defined in any of the above, wherein the step of placing the aerial root parts of at least one plant in a solvent for a predetermined length of time comprises placing about 150 g of plant material per liter of the solvent in the solvent for the predetermined length of time.

It is another object of the current invention to disclose the method as defined in any of the above, wherein the step of applying comprises applying by a method selected from a group consisting of: (a) spraying; (b) dipping; (c) coating; (d) contacting; (e) brushing; and any combination thereof.

It is another object of the current invention to disclose the method as defined in any of the above, wherein the step of applying comprises applying to a surface.

It is another object of the current invention to disclose the method as defined in any of the above, wherein the surface is selected from a group consisting of: (a) plant; (b) a building; and any combination thereof.

It is another object of the current invention to disclose the method as defined in any of the above, wherein the step of applying comprises applying directly to at least part of a plant.

It is another object of the current invention to disclose the method as defined in any of the above, wherein the step of applying comprises applying directly to at least part of a building.

It is another object of the current invention to disclose the method as defined in any of the above, wherein the step of applying comprises applying to an anti-insect net.

It is another object of the current invention to disclose the method as defined in any of the above, wherein the step of applying comprises applying an extract that comprises a component characterized by mass spectral peaks with m/z 223, 151, 96, and 81.

It is another object of the current invention to disclose the method as defined in any of the above, wherein the step of applying comprises applying an extract that comprises a component characterized by mass spectral peaks with m/z 94, 82, 67, 59, and 43.

It is another object of the current invention to disclose the method as defined in any of the above, additionally comprising a step of preparing an aqueous solution of the extract in water prior to the step of applying.

It is another object of the current invention to disclose the method as defined in any of the above, wherein the step of preparing an aqueous solution of the extract comprises preparing an aqueous solution in which the concentration of the extract is between 0.1% and 5% (w/v).

It is another object of the current invention to disclose the method as defined in any of the above, wherein the step of preparing an aqueous solution of the extract comprises preparing an aqueous solution in which the concentration of the extract is between 0.1% and 2.5% (w/v).

It is another object of the current invention to disclose the method as defined in any of the above, wherein the step of preparing an aqueous solution of the extract comprises preparing an aqueous solution in which the concentration of the extract is between 0.1% and 1.5% (w/v).

It is another object of the current invention to disclose the method as defined in any of the above, wherein the step of preparing an aqueous solution of the extract comprises preparing an aqueous solution in which the concentration of the extract is between 0.1% and 0.3% (w/v).

It is another object of the current invention to disclose the method as defined in any of the above, wherein the step of applying comprises applying about 60 ml of the aqueous solution per square meter of surface.

It is another object of the current invention to disclose the method as defined in any of the above, additionally comprising a step of compounding the extract with a polymer.

It is another object of the current invention to disclose the method as defined in any of the above, wherein the polymer is polyethylene.

It is another object of the current invention to disclose the method as defined in any of the above, wherein the step of compounding the extract with a polymer comprises coextruding the extract with the polymer.

It is another object of the current invention to disclose the method as defined in any of the above, additionally comprising a step of mixing the extract with a pesticide prior to the step of applying.

It is another object of the current invention to disclose the method as defined in any of the above, additionally comprising a step of introducing at least one natural enemy of the pest.

It is another object of the current invention to disclose the method as defined in any of the above, wherein the pests are selected from a group consisting of: (a) aphids; (b) tomato borers; (c) tomato leaf miners; (d) whiteflies; (e) thrips; (f) Red Spider mites; (g) Spider mites; (h) nitidulid beetles; (i) sap beetles; (j) red palm weevil; (k) cockroaches; (l) Leshimania; (m) sand flies; and any combination thereof.

It is another object of the current invention to provide a method for decreasing the rate of acquisition of resistance to a pesticide, comprising applying a mixture of the pesticide with an extract produced from at least one plant selected from a group consisting of: (a) *Achillea* spp; (b) *Varthemia iphionoides*; (c) *Haplophyllum turberculatum*; (d) *Pulicaria incise* (e) *Asteriscus graveolens*; (f) *Tanacetum sinaicum*; (g) *Verbascum* spp; (h) *Artemisia* spp; (i) *Ammi* visnaga; whereby at least some of the pests encountering the mixture are repelled by the extract in preference to ingesting the pesticide.

It is another object of the current invention to provide a pest repellent, comprising an extract produced from at least one plant chosen from a group consisting of: (a) *Achillea* spp; (b) *Varthemia iphionoides*; (c) *Haplophyllum turberculatum*; (d) *Pulicaria incise*; (e) *Asteriscus graveolens*; (h) *Tanacetum sinaicum*; (i) *Verbascum* spp; (j) *Artemisia* spp; (k) *Ammi visnaga*

It is another object of the current invention to disclose the pest repellent as defined in any of the above, wherein at least one plant is chosen from the group consisting of species of the genus *Achillea*.

It is another object of the current invention to disclose the pest repellent as defined in any of the above, wherein at least one plant is chosen from a group consisting of: (a) *Achillea santolina*; (b) *Achillea fragrantissima*; (c) *Achillea filipendulina* (d) *Achillea millefolium*; and any combination thereof.

It is another object of the current invention to disclose the pest repellent as defined in any of the above, wherein the extract is prepared according to the method of any one of claims 4-7.

It is another object of the current invention to disclose the pest repellent as defined in any of the above, wherein the extract comprises a component characterized by mass spectral peaks with m/z 223, 151, 96, and 81.

It is another object of the current invention to disclose the pest repellent as defined in any of the above, wherein the extract comprises a component characterized by mass spectral peaks with m/z 94, 82, 67, 59, and 43.

It is another object of the current invention to disclose the pest repellent as defined in any of the above, wherein the pest repellent comprises an aqueous solution containing between 0.1% and 5% (w/v) of the extract.

It is another object of the current invention to disclose the pest repellent as defined in any of the above, wherein the pest repellent comprises an aqueous solution containing between 0.1% and 2.5% (w/v) of the extract.

It is another object of the current invention to disclose the pest repellent as defined in any of the above, wherein the pest repellent comprises an aqueous solution containing between 0.1% and 1.25% (w/v) of the extract.

It is another object of the current invention to disclose the pest repellent as defined in any of the above, wherein the pest repellent comprises an aqueous solution containing between 0.1% and 0.3% (w/v) of the extract.

It is another object of the current invention to disclose the pest repellent as defined in any of the above, additionally comprising at least one pesticide.

It is another object of the current invention to disclose the pest repellent as defined in any of the above, wherein the extract is compounded with a polymer.

It is another object of the current invention to disclose the pest repellent as defined in any of the above, wherein the extract is coextruded with a polymer.

It is another object of the current invention to disclose the pest repellent as defined in any of the above, wherein the polymer is polyethylene.

It is another object of the current invention to disclose the pest repellent as defined in any of the above, wherein the repellent is adapted to repel pests selected from a group consisting of: (a) aphids; (b) tomato borers; (c) tomato leaf miners; (d) whiteflies; (e) thrips; (f) Red Spider mites; (g) Spider mites; (h) nitidulid beetles; (i) sap beetles; (j) red palm weevil; (k) cockroaches; (l) Leshimania (m) sand flies; and any combination thereof.

It is another object of the current invention to disclose the pest repellent as defined in any of the above, wherein the pest repellent is adapted for application to a surface.

It is another object of the current invention to disclose the pest repellent as defined in any of the above, wherein the surface is selected from a group consisting of: (a) plant; (b) a building; and any combination thereof.

It is another object of the current invention to disclose the pest repellent as defined in any of the above, wherein the plant extract comprises of a chemical compound selected from a group consisting of: (a) flavonoids; (b) saponins; and any combination thereof.

It is another object of the current invention to disclose the pest repellent as defined in any of the above, wherein the pest repellent is applied directly to at least part of a plant.

It is another object of the current invention to disclose the pest repellent as defined in any of the above, wherein the pest repellent is applied directly to at least part of a building.

It is another object of the current invention to disclose the pest repellent as defined in any of the above, wherein the pest repellent additionally contains additives selected from a group consisting of: (a) preservatives; (b) emulsifiers; (c) surfactants; (d) slow release additives; (e) UV additives; (f) gluing additives; (g) coloring agents; (h) fragrance; (i) diluents; (j) foaming agents; (k) stabilizers and any combination thereof.

It is another object of the current invention to disclose the pest repellent as defined in any of the above, wherein the pest repellent is encapsulated in a slow release device.

It is another object of the current invention to disclose the pest repellent as defined in any of the above, wherein the slow release device is comprised of polymers of glycolic acid or lactic acid.

It is another object of the current invention to disclose a kit adapted to repel pests; comprising: (a) a plant extract; (b) means for application of the plant extract; and (c) instructions for use, wherein the plant extract is produced from at least one plant chosen from a group consisting of *Achillea* spp, *Varthemia iphionoides*, *Haplophyllum turberculatum*, *Pulicaria incisa*, *Asteriscus graveolens*, *Tanacetum sinaicum*, *Verbascum* spp., *Artemisia* spp., and *Ammi visnaga*. The kit as defined above, wherein the means of application are selected from a group consisting of: (a) spray; (b) dropper (c) spreader; (d) applicator; and any combination thereof.

It is another object of the current invention to disclose the kit as defined in any of the above, wherein the kit additionally contains materials selected from a group consisting of: (a) stabilizers; (b) preservatives; (c) diluents; (d) color; (e) odor; (f) foaming agents; and any combination thereof.

It is another object of the current invention to disclose the kit as defined in any of the above, wherein the plant extract is diluted as defined above.

BRIEF DESCRIPTION OF THE DRAWINGS

The invention will now be described with reference to the drawings, wherein.

DETAILED DESCRIPTION OF THE PREFERRED EMBODIMENTS

Figure 1A:
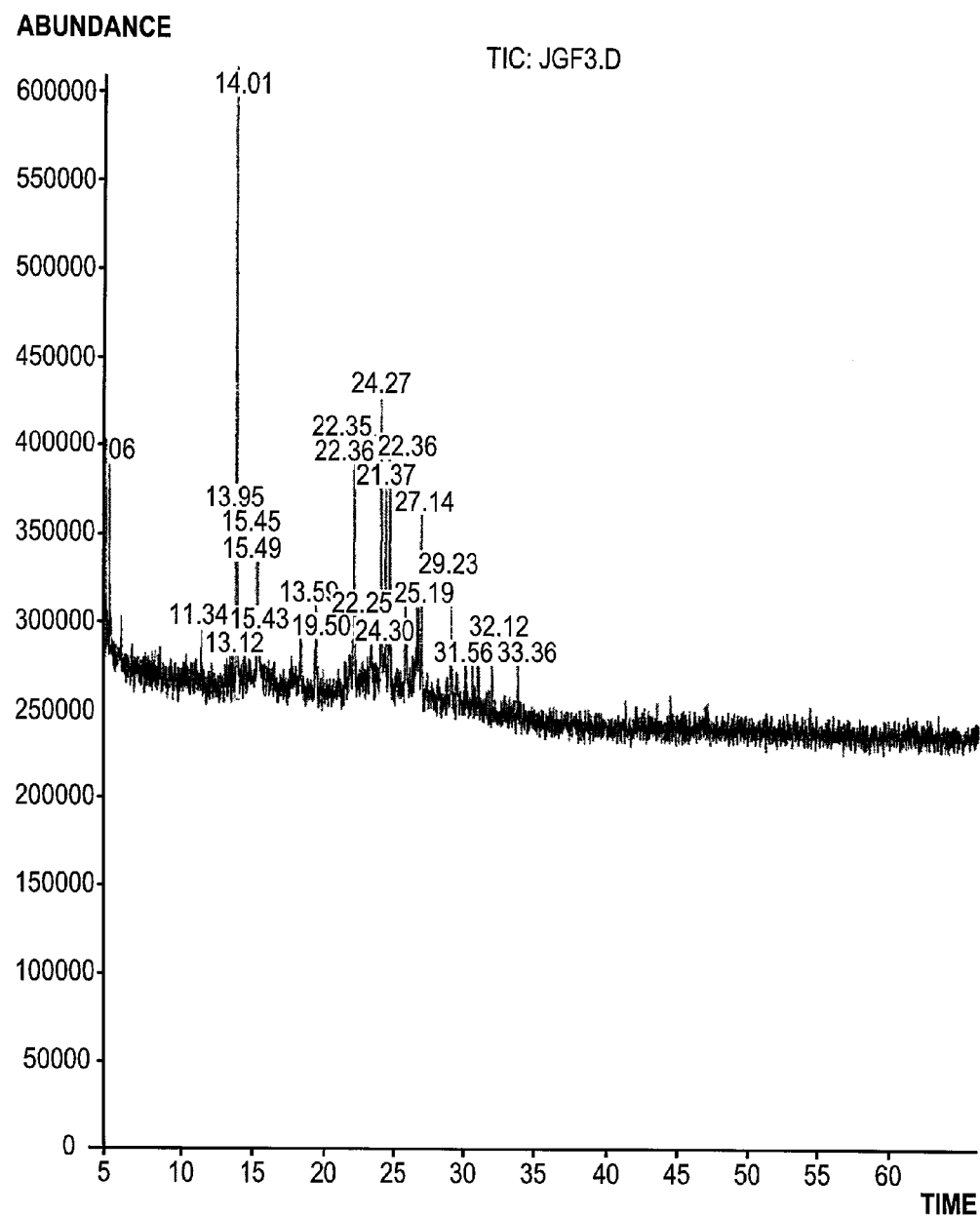
FIG. 1 presents representative gas chromatographs of the extract disclosed in the present invention.

In the following description, various aspects of the invention will be described. For the purposes of explanation, specific details are set forth in order to provide a thorough understanding of the invention. It will be apparent to one skilled in the art that there are other embodiments of the invention that differ in details without affecting the essential nature thereof. Therefore the invention is not limited by that which is illustrated in the figure and described in the specification, but only as indicated in the accompanying claims, with the proper scope determined only by the broadest interpretation of said claims.

As used herein, the term "about" refers to a range of ±25% relative to the nominal quantity.

The term "pesticide" refers hereinafter to a chemical or biological agent that through its effect incapacitates and/or kill pests.

The term "repellent" refers hereinafter to a substance applied to a surfaces which discourages pests from landing or climbing on that surface.

The term "pest" refers hereinafter to arachnoids, parasites or insects that are detrimental to humans and/or crops and/or plants The term "saponin" refers herein after to a class of chemical compounds found in particular abundance in various plant species. More specifically, they are amphipathic glycosides grouped, in terms of phenomenology, by the soap-like foaming they produce when shaken in aqueous solutions, and, in terms of structure, by their composition of one or more hydrophilic glycoside moieties combined with a lipophilic triterpene derivative.

The term "flavonoid" refers hereinafter to a large family of polyphenolic compounds synthesized by plants that have a common chemical structure.

The term "slow release device" refers hereinafter to a device that slowly releases the active ingredient. In pesticides slow release might have significance in reducing the amount of pesticides used as they will become more efficient and less costly.

The basis of the invention herein disclosed is a plant extract composition derived from a plant chosen from the group consisting of *Achillea* spp., *Varthemia iphionoides*, *Haplophyllum turberculatum*, *Pulicaria incisa*, *Asteriscus graveolens, Tanacetum sinaicum, Verbascum* spp., *Artemisia* spp., and *Ammi visnaga*, or a combination of such extracts. In preferred embodiments, the composition comprises an extract of a plant of genus *Achillea*. In the most preferred embodiments of the invention, it comprises an extract of a plant chosen from the group consisting of *Achillea santolina, Achillea fragrantissima, Achillea millefolium* and *Achillea filipendulina*.

It is suggested that some of the compounds responsible for the repelling effect belong to the Flavonoids and/or Saponins.

The repellent is found useful for protecting crops against damages caused by pests. The main pest groups, families and species that the plant extract of the present invention repels are: aphids, tomato borers, tomato leaf miners, whiteflies, thrips, Red Spider mites, Spider mites, nitidulid beetles, sap beetles, red palm weevils, cockroaches, Leshimania and sand flies. The plant extract may also be beneficial against other species of pests.

The plant extract was also found to be useful for eliminating pests inside houses. It has been shown that spraying a surface with a house with the plant extract practically eliminated the presence of cockroaches, sand flies and Leishmania.

In typical embodiments of the invention, the extract is prepared by placing plant material (in preferred embodiments, aerial parts of the plants are used) in a solvent until at least a portion of the active component or components of the plant has been extracted into the solvent. In preferred embodiments of the invention, the solvent is ethanol; in the most preferred embodiments, 96% ethanol is used. In typical embodiments of the invention, about 150 g of plant material is used per liter of solvent, and the plant material is placed in the solvent for about 24 h. The solid plant material is then removed (preferably by filtration), and the liquid remaining, comprising the plant extract, is then used as a pest repellent.

Figure 1B:
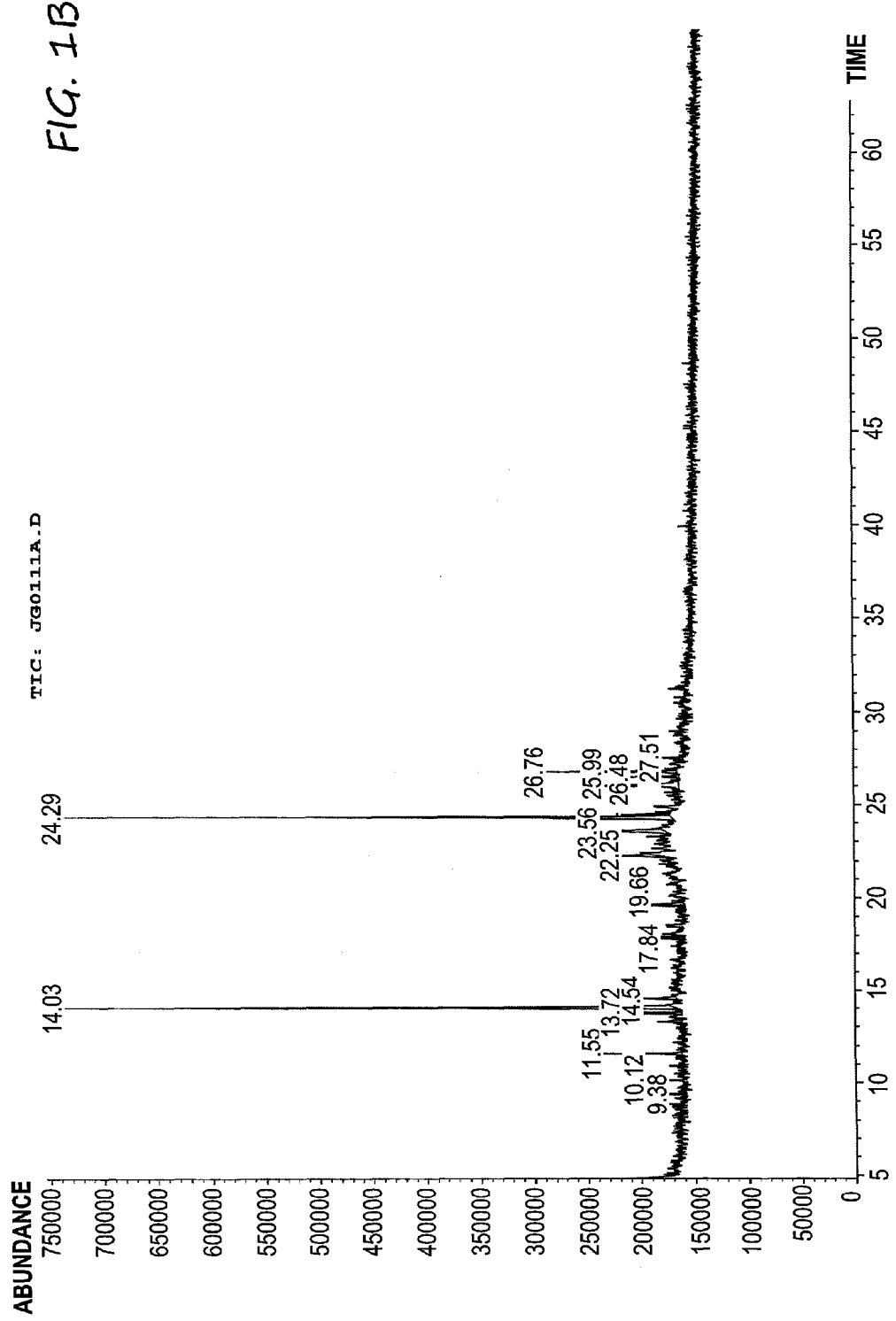

In preferred embodiments, the entire extract is used. The extracts used have been characterized, at least in part, by gas chromatography and mass spectrometry. Reference is now made to FIG. 1, which shows typical gas chromatographs (GCs) of extracts of *Achillea* sp obtained by the above method. The GCs shown in the figure were obtained using a Hewlett-Packard G1800A GCD system fitted with a 5% phenylmethylsiloxane (HP-5MS) capillary column (30 m length, 0.25 mm internal diameter). Splitless injection was used; the helium carrier gas flow rate was 1 ml/min, and the solvent delay was 4.8 min. The detector was heated to 280° C. and the injector to 250° C. The temperature program was as follows: the column was held at a constant 50° C. for 4 min. The temperature was then raised at a rate of 8° C./min until it reached 280° C., where it was held constant for 60 min.

Figure 2A:
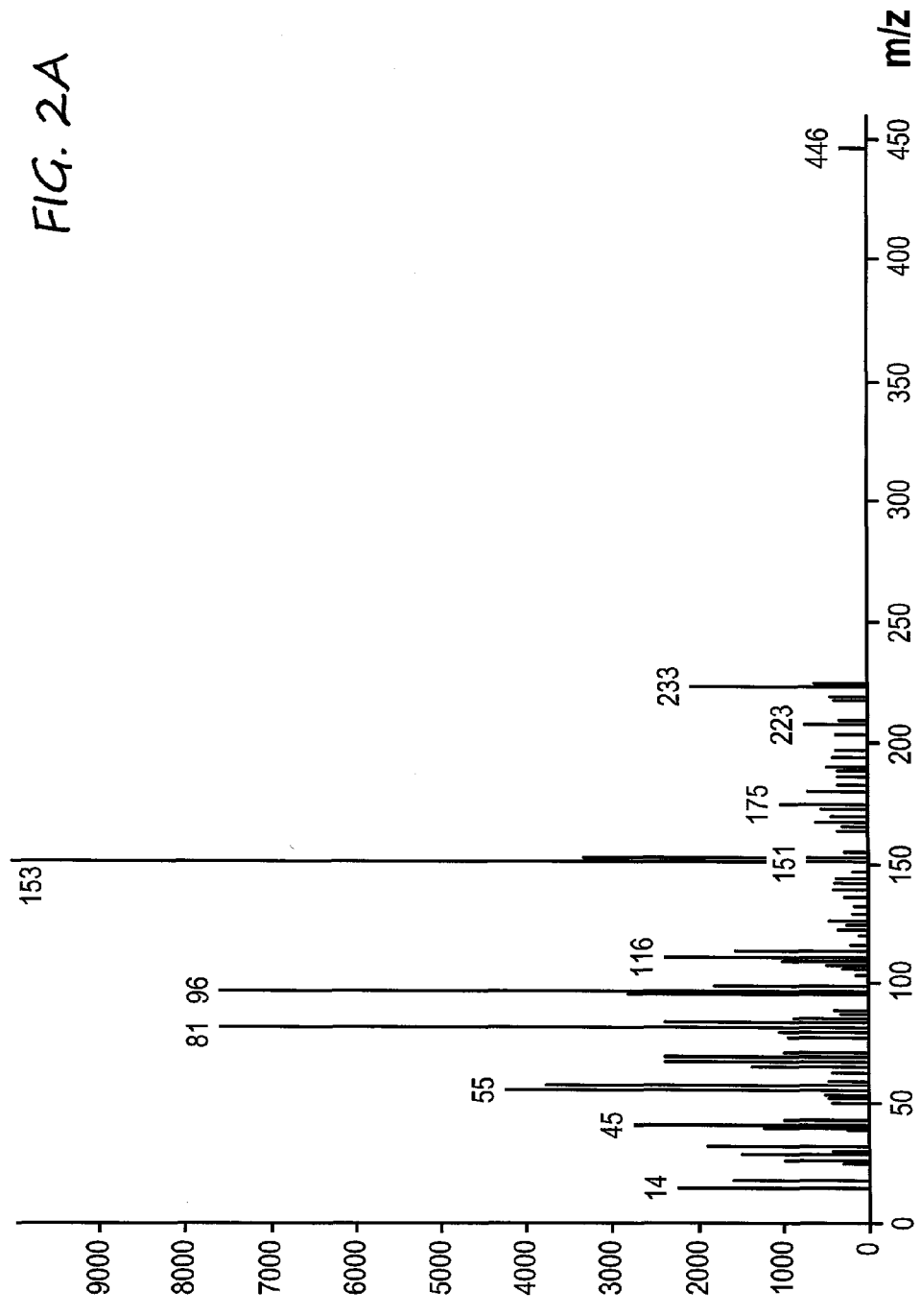
FIG. 2 presents representative mass spectra of particular fractions of the extract obtained by gas chromatography.
Figure 2B:
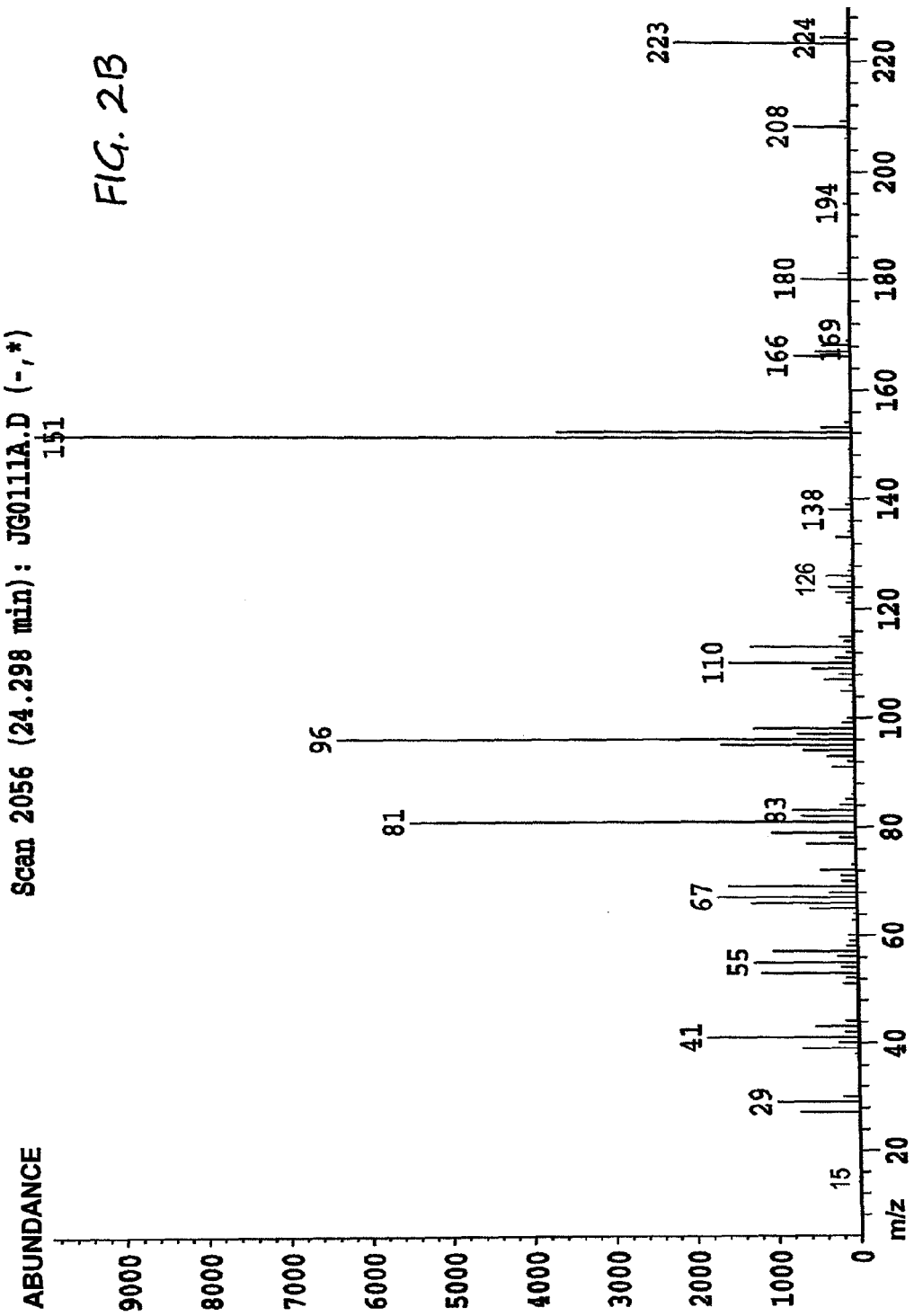
Figure 2C:
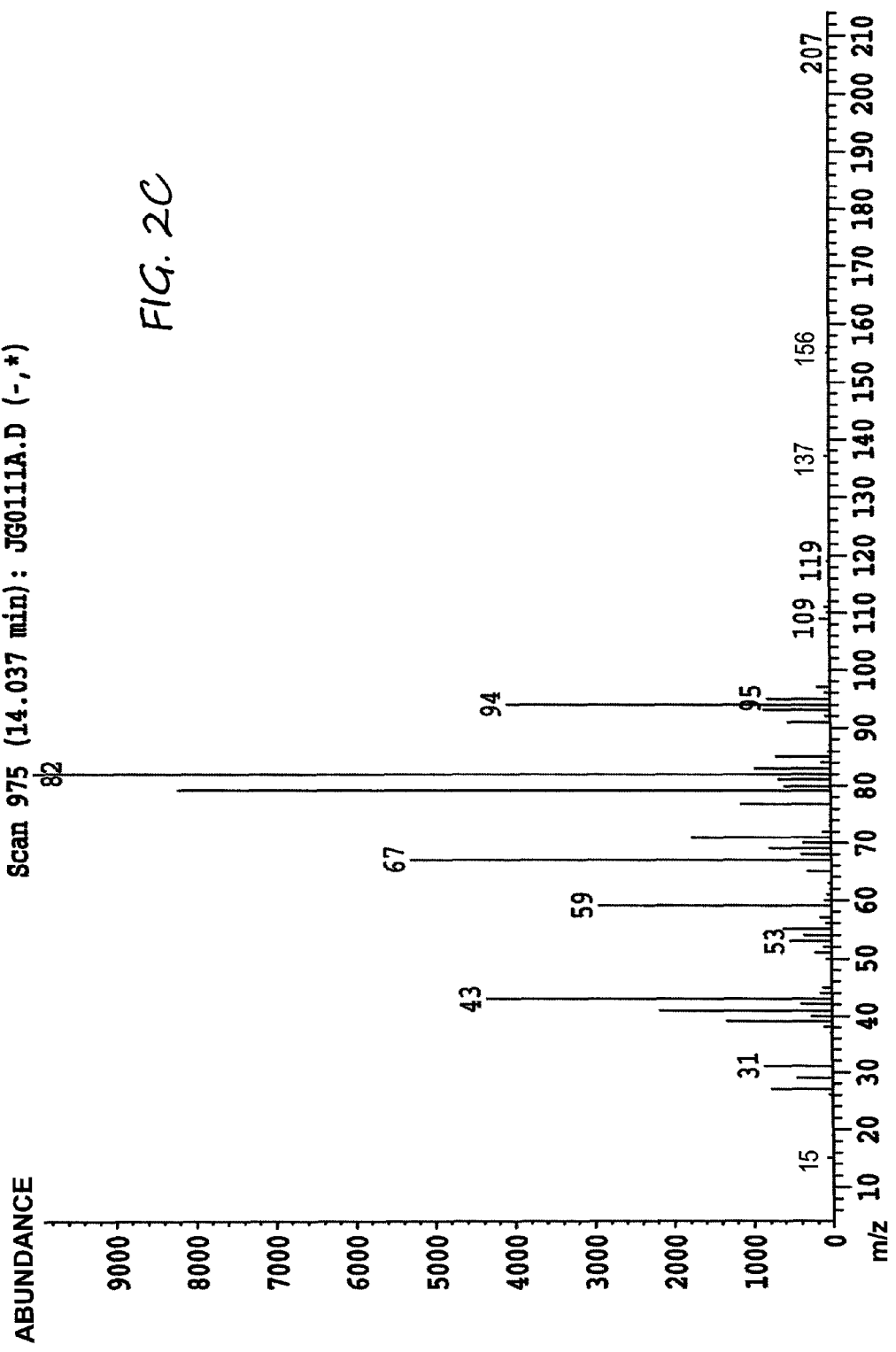

Reference is now made to FIG. 2, which shows mass spectra of two of the fractions obtained from the GC. FIGS. 2A and 2B show mass spectra of the fraction obtained at 24.220 min in the GC shown in FIG. 1A and at 24.298 min in the GC shown in FIG. 1B. The mass spectrum shows major peaks (in order of decreasing intensity) with m/z 151, 81, and 96, and a parent peak at 223. The mass spectrum shown in FIG. 1A also appears to show a dimer peak with m/z 446. FIG. 2C shows a mass spectrum of the fraction eluted at 14.008 minutes in the GC shown in FIG. 1A. The mass spectrum has major peaks (in order of decreasing intensity) with m/z 82, 67, 43, 94, and 59. Without wishing to be bound by theory, it appears that the active ingredients in the extracts are contained within this fraction.

According to the method for repelling pests disclosed herein, the repellent prepared as described herein is applied to a surface or volume where it is desired that pests be removed or into which it is desired that pests not enter. The repellent may be applied on the target area by any convenient means known in the art; non-limiting examples include dipping, coating, contacting, spraying, and brushing, depending on the nature of the target area. For example, if the target area is a flower or fruit, dipping may be most efficient; for application to surfaces, spraying may be the preferred method. In typical embodiments, the extract is sprayed on a target surface; in preferred embodiments, it is sprayed on the target surface in the form of an aqueous solution. In more preferred embodiments, the aqueous solution contains no more than 5% (w/v) of extract. In the most preferred embodiments, about 60 ml of a solution containing 1-1.5% (w/v) of extract is sprayed per square meter of surface. The extract may be sprayed on plants, netting, or any other compatible surface to repel pests or lower the attraction of pests to the target area.

In some embodiments of the invention, the extract is diluted in an appropriate solvent (e.g. water) prior to its application. In some preferred embodiments of the invention, the extract is be diluted to form a solution that is 5.0% extract (w/v). In other preferred embodiments of the invention, the extract is diluted to form a solution that is 2.5% extract (w/v). In yet other preferred embodiments of the invention, the extract is diluted to form a solution that is 0.3% extract (w/v).

While the extract is an effective repellent against a wide variety of pests, it has been found to be particularly effective against aphids, tomato borers, tomato leaf miners, whiteflies, and thrips.

In some embodiments of the invention, the extract produced as disclosed above is incorporated into a polymer, thus forming an pest-repellent polymer. The compounding of the extract and polymer may be performed by any means known in the art. One non-limiting example of such compounding is a polyethylene film or sheet coextruded with the extract. In typical embodiments, the coextruded film or sheet contains between about 0.1% and 10% extract by weight. The coextruded film or sheet may also include other pest repellents or pesticides in amounts of between 0.1% and 20% by weight.

As was mentioned above, use of pesticides has been known to lead to resistance. It is therefore within the scope of the invention to disclose a method for slowing or eliminating pesticide resistance. In this method, the repellents disclosed in the present invention are mixed with a known pesticide, and this mixture applied as above. Typical mixtures comprise between 0.1% and 10% repellent by weight and between 0.1% and 20% pesticide by weight. Since a significant fraction of the pests will be repelled by the repellent without contacting or ingesting an effective dose of the pesticide, the likelihood that mutations that enable the pests to metabolize the pesticide will spread through the population is lowered.

The invention will now be described by a series of illustrative examples. These examples are intended to enable one skilled in the art to make and use the invention, and are not intended to define or limit the invention.

EXAMPLE 1

Two 3 cm×3 cm squares of red cabbage were placed in a Petri dish. One of the pieces of cabbage was treated with a diluted solution of the extract prepared as described above, and the other with a 5% (w/v) solution of ethanol in water. In three separate experiments, solutions of extract diluted to 5%, 2.5%, and 0.3% (w/v), respectively, were tested. Each experiment was performed three times. Fifteen adult female thrips were placed in each Petri dish. The leaves were observed three days after the commencement of the experiment. Orange or white areas in the cabbage indicate consumption by the thrips.

Cabbage leaves treated with a 5% aqueous solution of the extract were completely free of any sign of consumption by the thrips, while all of the control leaves showed signs of having been attacked by the thrips.

In a second experiment, red cabbage leaves were treated with Neem tree extract, which has been reported to have pesticidal and pest repellent activity, and all of the leaves so treated showed evidence of having been attacked by the thrips.

EXAMPLE 2

Figure 3:
FIG. 3 presents a photograph showing the experimental setup of a demonstration of the efficacy of the materials and methods disclosed herein; and, FIG. 4 shows a photograph of the setup experiments designed to test the efficacy of the materials and methods disclosed herein when applied to netting, and graphs plotting results of the experiments.

Approximately 20 chive plants were placed in planters in a greenhouse. The plants were covered with a 40-mesh anti-insect net. Reference is now made to FIG. 3, which presents a photograph of the experimental setup. Half of the planters were coated with 60 ml/m2 of the pest-repellent composition disclosed herein comprising 1.25% by weight of *Achillea* extract, and the other half were coated with an ethanol-water mixture as a control. After approximately two weeks, the plants were checked for the number of thrips. After two weeks, the plants treated according to the invention herein disclosed averaged 5 thrips per plant infestation, while the control plants averaged 60 thrips per plant. Thus, the material and method of the present invention led to a >90% reduction in the amount of thrip infestation relative to the control sample.

EXAMPLE 3

Figure 4A:
Figure 4B:
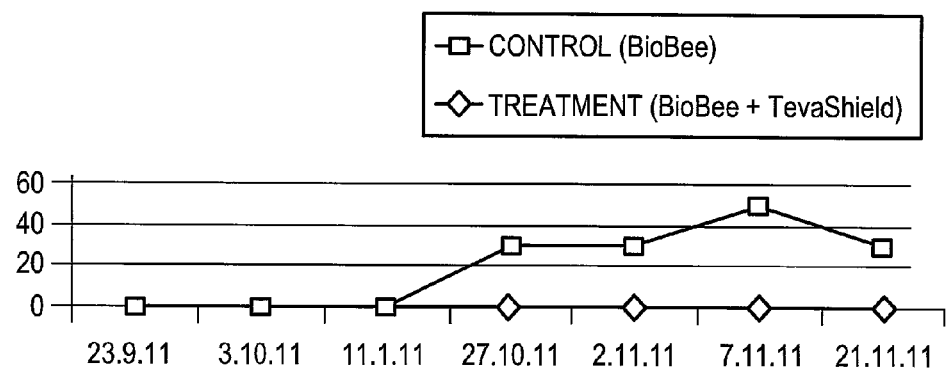
Figure 4C:
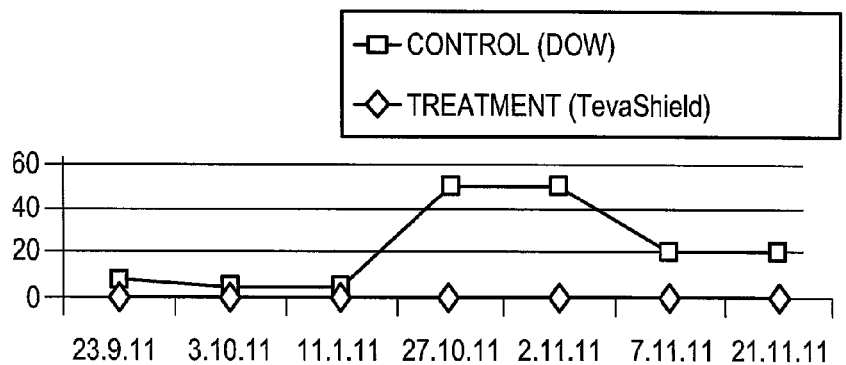

An industrial-scale experiment was performed in cooperation with Bio-Bee (Sde Eliahu, Israel) in a greenhouse in which organic peppers were being raised. The greenhouse walls, made of net of 850 m length, were sprayed with a composition containing *Achillea* extract (1% w/v, 60 ml/m2) according to the methods disclosed herein fortnightly for six weeks. As a control, the walls of a second greenhouse, made of similar netting, were left untreated. Reference is now made to FIG. 4A, which presents a photograph illustrating the experimental setup. In the control and the experimental greenhouses, the plants were treated by application of a Western flower thrip predator according to technology developed by Bio-Bee or by application of a commercially available spinosad-containing pesticide (Tracer® manufactured by Dow Chemicals). Reference is now made to FIGS. 4B and 4C, which present graphs of the experimental results (percentage of the plants infested by thrips as a function of time). While in both those experiments in which the Bio-Bee predator and those in which the spinosad-containing pesticide were used as controls, approximately 50% of the control plants showed signs of thrip infestation, none of the plants in the experimental greenhouse showed any sign of thrip infestation, thus demonstrating the improved efficacy of the present invention used in conjunction with Bio-Bee's technology relative to the use of Bio-Bee's technology alone.

EXAMPLE 4

A number of cotton seedlings were planted in each of two planters, and placed within a single cage. The seedlings in one of the planters were treated with *Achillea* extract according to one embodiment of the present invention (1% w/v, 60 ml/m2), while the second was left untreated as a control. Approximately 100 whiteflies were released into the cage, and after 36 hours, the number of whiteflies in each of the two planters was measured. Three independent repetitions of the experiment were performed. On average, >80 whiteflies were found in the planters containing the control plants, while <5 were found in the planters containing the treated plants, i.e. the invention disclosed herein provided a >90% reduction in the amount of whitefly infestation.

EXAMPLE 5

Six planters containing tomato plants were covered with a 40 mesh net that contained approximately 75 holes of diameter of about 5-10 mm. The nets covering three of the planters were coated with *Achillea* extract according to the invention herein disclosed and dried in the sun for about half an hour, while the remaining three were coated with an ethanol/water solution as a control. The six planters were introduced into a container containing about two dozen tomato leaf miners (Tuta absoluta). The planters were checked for tomato leaf miner infestation 15 days after the commencement of the experiment. Dead tomato leaf miners were found in each of the control planters (three in each of two of the planters, and one in the third), and all of the plants therein showed evidence of having been eaten. Neither dead leaf miners nor evidence of attack by leaf miners were found in the experimental plants.

EXAMPLE 6

Figure 5A:
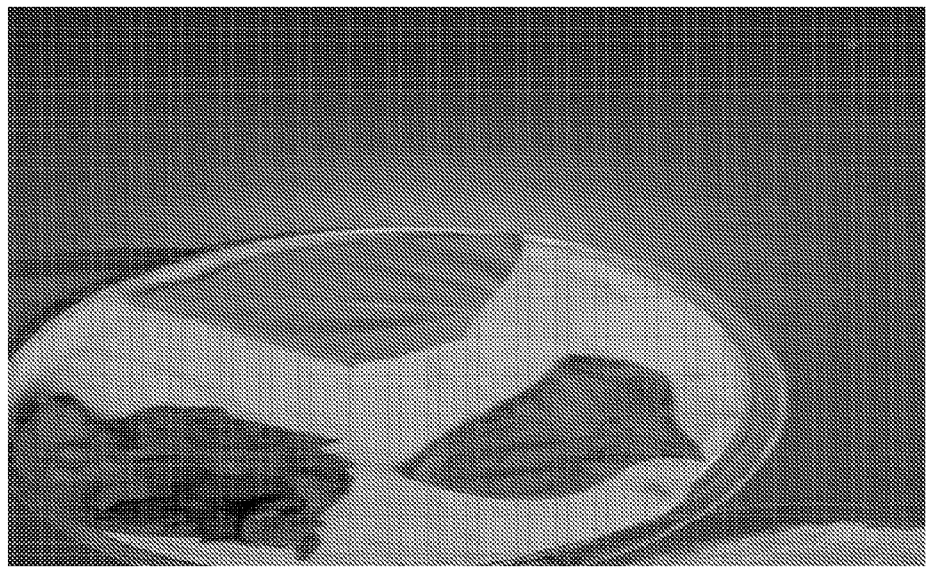
FIG. 5 shows a photograph of the setup experiments designed to test the efficacy of the materials against spider mites when applied to leaves, and graphs plotting results of the experiments.
Figure 5B:
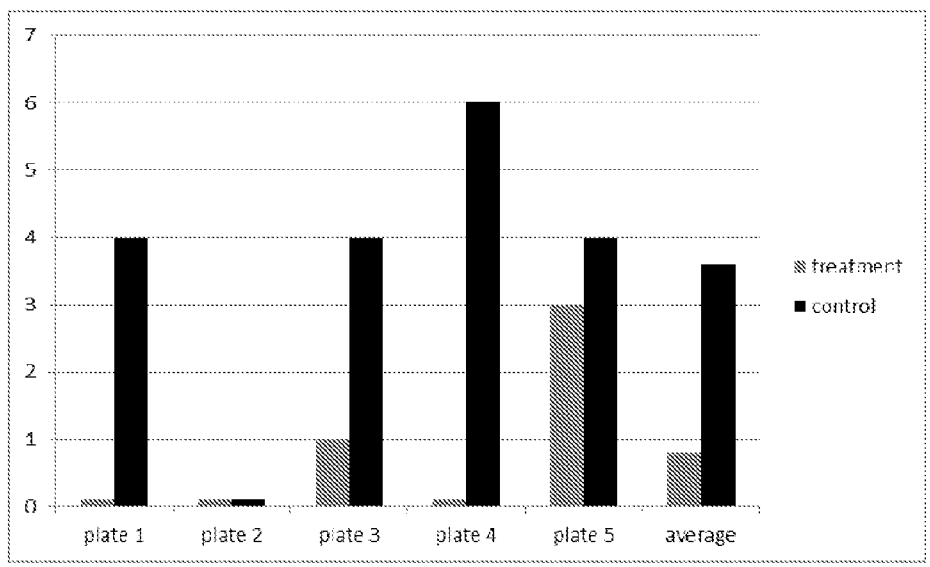

An experiment was conducted in collaboration Jacob Nakash, Bet Shean Valley, December 2012.
A Bell pepper leaf was treated with EdenShield product (*Achillea* extract in a concentration of 20 mg/ml) concentration, and placed in a petri dish with a non-treated leaf and an additional leaf infested with red spider mites. Five identical dishes were prepared as described. The dishes were monitored after 3 days to count how many red spider mites infested the treated and control leaves.
Reference is now made to FIG. 5A, which presents a photograph illustrating the experimental setup.
FIG. 5B graphically presents the results of the described experiment. It can be clearly seen that after three days the amount of red spider mites in the leaf treated with EdenShield product were significantly less than their amount in the untreated leaf.

EXAMPLE 7

Figure 6A:
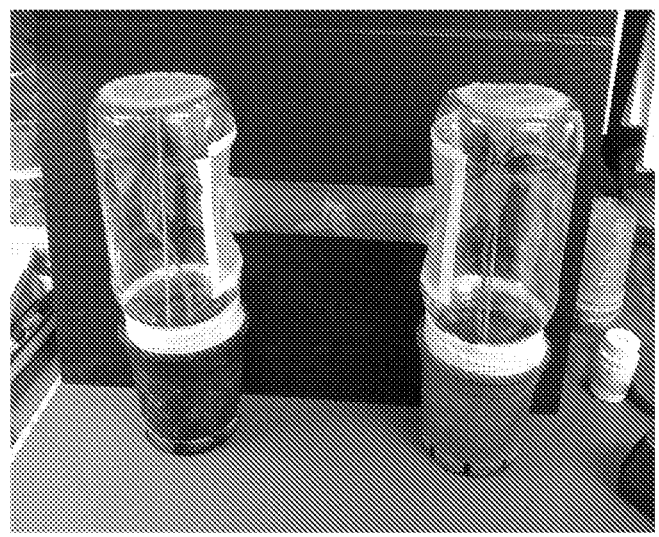
FIG. 6 shows a photograph of the setup experiments designed to test the efficacy of the materials against red spider mites when applied to net-covers, and graphs plotting results of the experiments.
Figure 6B:
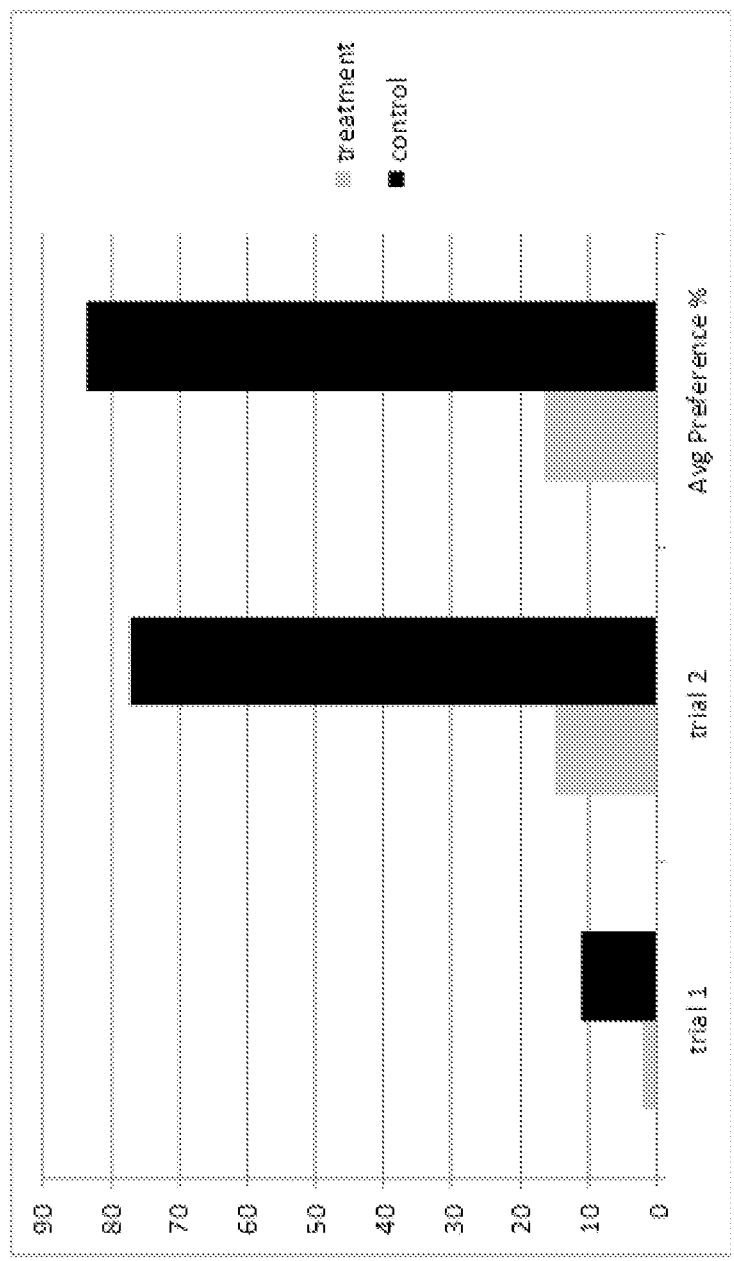

An experiment was conducted in collaboration Jacob Nakash, Bet-Shean Valley, December 2012.
Two pots with one bell pepper plant in each were covered with an anti pest net and interconnected by a tube into which red spider mites were introduced. The spider mites are then free to choose to which pot they will turn. The net cover of one pot is treated with the EdenShield product (*Achillea* extract in a concentration of 20 mg/ml) by spraying the product on to the net cover and the other pot serves as a control and therefore its net is not treated with any material. Two experiments were carried out utilizing the described experimental setup with only a difference in the number of spider mites that were introduced into the tube.
Reference is now made to FIG. 6A, which presents a photograph illustrating the experimental setup.
Reference is now made to FIG. 6B, which graphically describes the amount of spider mites in each of the pots. It can be seen that although the number of spider mites introduced in each experiment was different, the percentage of their preference was similar.

EXAMPLE 8

An experiment was conducted in collaboration with Jacob Nakash, Bet Shean Valley, carried out in Kibutz Shluchot, and Sde-Elyahu, Bet Shean Valley, Israel.
In one experiment conducted in Kibutz Shluchot four orchard trees selected for the trial were of the Hatrawi species and were 6-7 years old containing each about 15-20 bunches.
All bunches on the orchards were covered by 10 mesh plastic nets as normal agricultural practice.
On the 20 Sep. 2012 four bunches in each of the four trees selected for the experiment were additionally covered with a cotton net with 10 mm openings immersed in the plant extract solution before being placed. The bunches are not covered with the cotton net served as control.

On the 10 Oct. 2012 (20 days following the covering with the cotton net) the nets were sprayed with plant extract solution.

On the 18 Oct. 2012 (8 days following the spraying the nets with the plant extract solution) the treated bunches were sampled for nitidulid beetles, and compared with an equal amount of bunches from untreated trees.

Figure 7A:
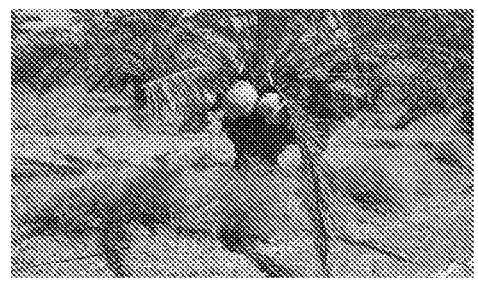
FIG. 7 shows a photograph of the setup experiments designed to test the efficacy of the materials against nitidulid beetles when the extract is applied to cotton nets of orchard trees, and graphs plotting results of the experiments.

Reference is now made to FIG. 7A, which presents a photograph illustrating the experimental setup in Kibutz Shluchot.

In a second experiment conducted in Kibutz Sde Eliyahu, two 15 years old orchard trees selected for the trial were of the Halawi specie and contained about 18 bunches.

All bunches on the orchards were covered by 10 mesh plastic nets as normal agricultural practice.

Similar to the experiment in Kibutz Shluchot:

On the 20 Sep. 2012 all bunches on one tree were additionally covered with a cotton net with 10 mm openings immersed in the plant extract solution before being placed. The bunches of the second tree were not covered with the cotton net and served as control for the experiment.

On the 10 Oct. 2012 (20 days following the covering with the cotton net) the cotton nets were sprayed with plant extract solution.

On the 24 Oct. 2012 (2 weeks following the spraying the nets with the plant extract solution) the treated bunches were sampled for nitidulid beetles, and compared with an equal amount of bunches from the untreated tree.

Figure 7B:

Reference is now made to FIG. 7b, which presents a photograph illustrating the experimental setup in Kibutz Sde Eliyahu.

Figure 7C:
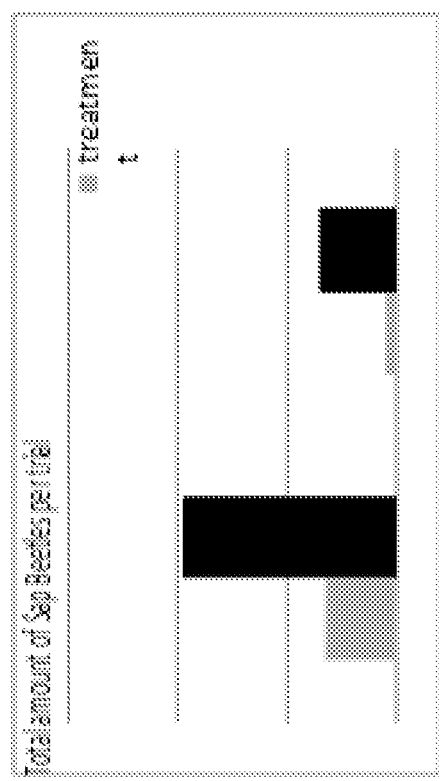

Reference is now made to FIG. 7C which summarizes in a chart the results of the experiment. It is shown that the treatment lowered the average amount of nitidulid beetles by 66% in Kibutz Shluhot, and by 88% in Kibutz Sde Eliyahu.

EXAMPLE 9

A specific thin layer chromatography (TLC) experiment for detecting flavonoids was carried out on *Achillea Fragrantissima* extracts with different bioassay activities. The bioassay activity was determined as described in Example 6, using thrips instead of spider mites.

The samples were placed on 25 Aluminium sheets 20×20 covered with TLC Silica gel 60 F254 that served as the stationary phase. The mobile phase was composed of ethyl acetate, formic acid, acetic acid and water in a relation of 100:11:11:27, respectively.

The sample was stained with 1% methanol solution of Diphenylboryloxyethylamine followed by 5% ethanol solution of polyethylenglycol-4600 and then dried at room temperature.

Visualization was done under UV-366 nm.

Figure 8:
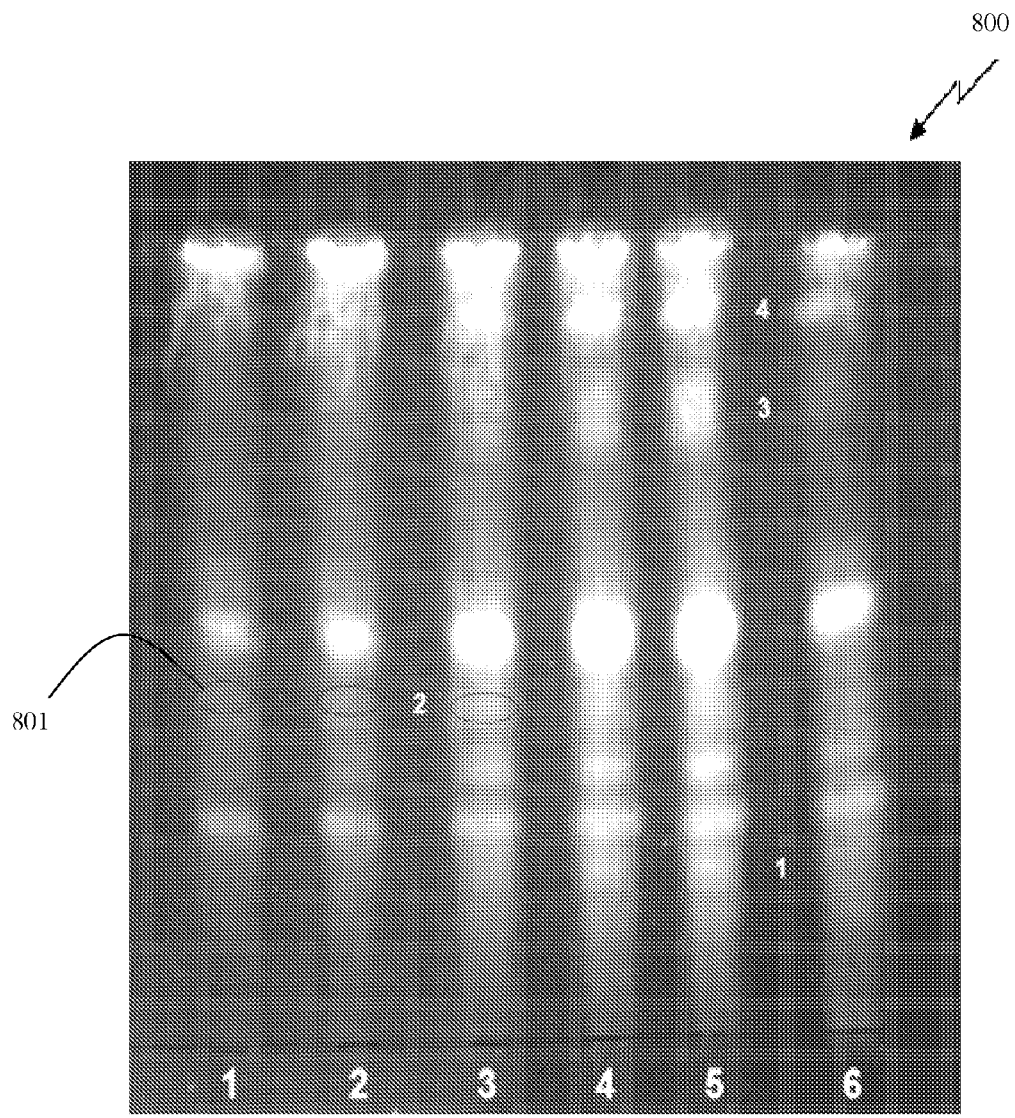
FIG. 8 shows the result of a TLC experiment for detecting Flavonoids.

Reference is now made to FIG. 8 which presents the results of the TLC experiment:

Lane 1 is a "gold standard" prepared from solid residue of the extraction procedure; Lane 2—plant extraction done in room temperature (RT) for 3 hours in 96% Ethanol; Lane 3—plant extraction done in boiling 96% Ethanol for 1 hour (first extraction); Lane 4—plant extraction done in boiling 96% Ethanol for 1 hour (second extraction); Lane 5—plant extraction done in boiling 96% Ethanol for 1 hour (third extraction); Lane 6—25% ethanol left in RT for 3 hours.

It can be seen in FIG. 8 that the compound at Rf 0.4 (801) is absent in the sample in lane 6 and is presented in minor concentrations in sample in lanes 4-5.

The samples in lanes 1-3 were stable in the different bioassays.

In the case of the step extraction (samples in lanes 3-%) the repellent activity was significantly decreased in each consecutive extract. Sample 6 had no activity in the bioassays.

It is apparent that there is a connection between the content of the material in Rf 0.4 and the repellent activity of the extract.

EXAMPLE 10

A specific thin layer chromatography (TLC) experiment for detecting saponins content in *Achillea Fragrantissima* extracts with different activity in bioassay. The bioassay activity was determined as described in Example 6, using thrips instead of spider mites.

The samples were placed on 25 Aluminium sheets 20×20 covered with TLC Silica gel 60 F254 that served as the stationary phase. The mobile phase was composed of chloroform, acetic acid; methanol and water in a relation of 64:32:12:8, respectively.

The sample was stained with Anisaldehyde-Sulfuric Acid (0.5 ml Anisaldehyde is mixed with 10 ml glacial acetic acid, 85 ml methanol and 5 ml concentrated $H_2SO_4$) and then dried at 100° C. for 2-3 min.

Visualization was done under UV-366 nm.

Figure 9:
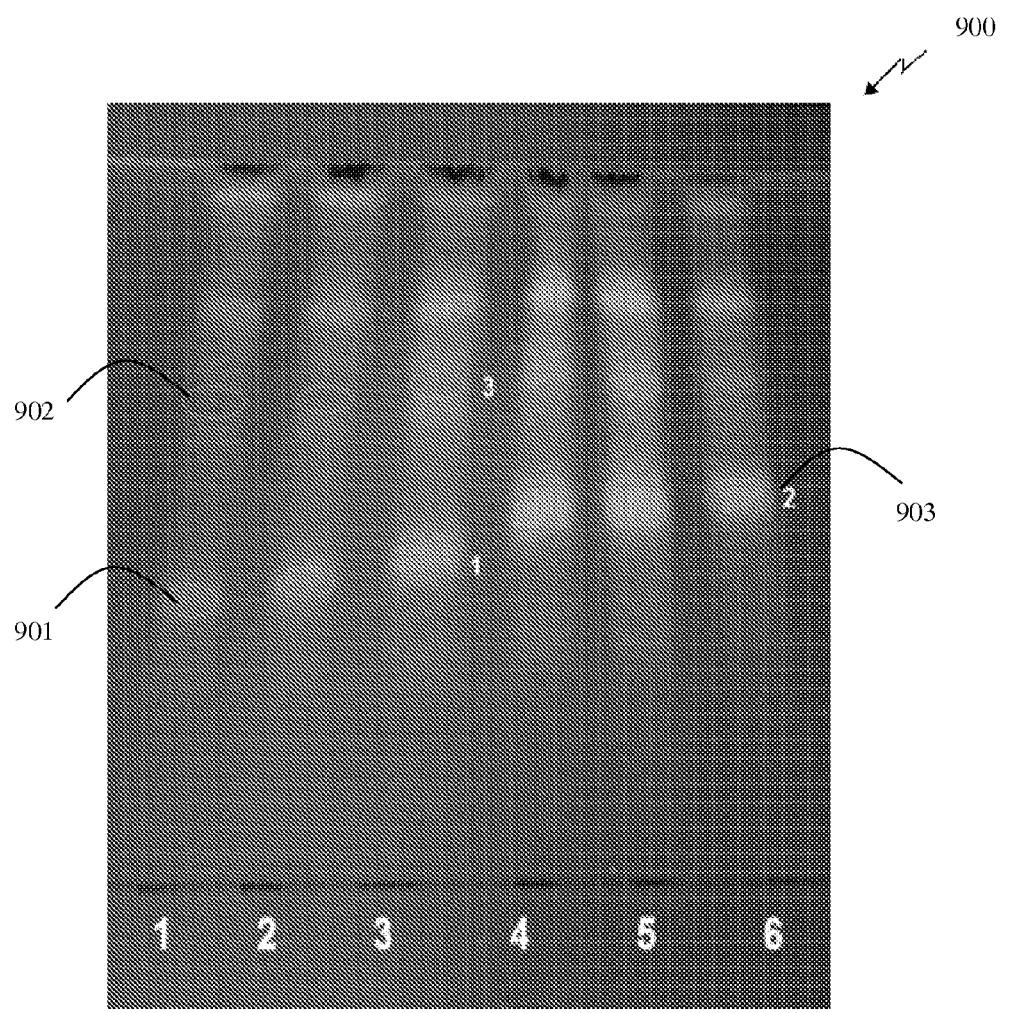
FIG. 9 shows the result of a TLC experiment for detecting Saponins.

Reference is now made to FIG. 9 which presents the results of the TLC experiment:

Lane 1 is a "gold standard" prepared from solid residue of the extraction procedure; Lane 2—plant extraction was done in room temperature (RT) for 3 hours in 96% Ethanol; Lane 3—plant extraction was done in boiling 96% Ethanol for 1 hour (first extraction); Lane 4—plant extraction was done in boiling 96% Ethanol for 1 hour (second extraction); Lane 5—plant extraction was done in boiling 96% Ethanol for 1 hour (third extraction); Lane 6—25% ethanol left in RT for 3 hours.

The compound with Rf 0.35 (901) and the compound with Rf 0.56 (902) are present only in active extracts and are responsible for activity of samples #1, 2 and 3. Compound 2 with Rf 0.44 (903) is present only in non-active extracts.

The invention claimed is:

1. A method for repelling pests, comprising applying to a surface a composition comprising an extract produced from *Achillea fragrantissima* plant; wherein said pests are selected from a group consisting of: (a) aphids; (b) tomato borers; (c) tomato leaf miners; (d) whiteflies; (e) thrips; (f) Red Spider mites; (g) Spider mites; (h) nitidulid beetles; (i) sap beetles; (j) red palm weevil; (k) cockroaches; (l) Leshimania (m) sand flies; and any combination thereof;

said extract comprises a component characterized by mass spectral peaks consisting of m/z 94, 82, 67, 59, and 43; and said plant extract comprises chemical compounds selected from a group consisting of: (a) flavonoids and (b) saponins.

2. The method according to claim 1, wherein said extract comprises a component characterized by mass spectral peaks of (a) m/z 223, 151, 96, and 81.

3. The method according to claim 1, wherein said pest repellent comprises an aqueous solution containing a concentration of extract selected from a group consisting of (a) between 0.1% and 5% (w/v) (b) between 0.1% and 2.5% (w/v) (c) between 0.1% and 1.25% (w/v) (d) between 0.1% and 0.3% (w/v); and any combination thereof.

4. The pest repellent method according to claim 1, wherein said composition additionally comprising at least one pesticide.

5. The method according to claim 1, wherein said extract is compounded or coextruded with a polymer.

6. The method according to claim 1, wherein said surface is selected from a group consisting of: (a) plant; (b) a building; and any combination thereof.

7. The method according to claim 1, wherein said composition additionally contains additives selected from a group consisting of: (a) preservatives; (b) emulsifiers; (c) surfactants; (d) slow release additives; (e) UV additives; (f) gluing additives; (g) coloring agents; (h) fragrance; (i) diluents; (j) foaming agents; (k) stabilizers and any combination thereof.

8. The method according to claim 1, further comprising a step of encapsulating said composition in a slow release device.

* * * * *